United States Patent
Barron et al.

(10) Patent No.: US 7,671,055 B2
(45) Date of Patent: Mar. 2, 2010

(54) INSECTICIDAL 3-(DIHALOALKENYL) PHENYL DERIVATIVES

(75) Inventors: Edward J. Barron, Trenton, NJ (US); Y. Larry Zhang, Kendall Park, NJ (US); Frank J. Zawacki, Yardley, PA (US); John W. Lyga, Basking Ridge, NJ (US); George Theodoridis, Princeton, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 11/577,667

(22) PCT Filed: Oct. 20, 2005

(86) PCT No.: PCT/US2005/038226

§ 371 (c)(1),
(2), (4) Date: Apr. 24, 2008

(87) PCT Pub. No.: WO2006/047438

PCT Pub. Date: May 4, 2006

(65) Prior Publication Data

US 2008/0261993 A1  Oct. 23, 2008

Related U.S. Application Data

(60) Provisional application No. 60/621,380, filed on Oct. 22, 2004.

(51) Int. Cl.
| | |
|---|---|
| C07D 241/04 | (2006.01) |
| C07D 307/78 | (2006.01) |
| C07D 401/04 | (2006.01) |
| C07C 43/205 | (2006.01) |
| A61K 31/09 | (2006.01) |
| A61K 31/451 | (2006.01) |
| A61K 31/496 | (2006.01) |

(52) U.S. Cl. .............. 514/253.01; 514/255.03; 514/318; 514/330; 514/473; 514/720; 544/360; 544/383; 544/386; 544/394; 546/194; 546/226; 549/466; 568/646

(58) Field of Classification Search .............. None
See application file for complete search history.

(56) References Cited

U.S. PATENT DOCUMENTS

| 4,784,682 A | 11/1988 | Förster et al. |
| 5,922,880 A | 7/1999 | Sakamoto et al. |
| 6,410,578 B1 | 6/2002 | Bouvier et al. |

OTHER PUBLICATIONS

International Search Report for International Application No. PCT/US05/38226, United States Patent and Trademark Office, Alexandria, Virginia, mailed on Sep. 18, 2006.

*Primary Examiner*—Fiona T Powers

(57) ABSTRACT

Certain novel 3-(dihaloalkenyl)phenyl derivatives have unexpected insecticidal activity. These compounds are represented by formula (I), where R through $R^5$, a, b, D, E, G and U are fully described herein. In addition, compositions comprising an insecticidally effective amount of at least one compound of formula (I), and optionally, an effective amount of at least one of second compound, with at least one insecticidally compatible carrier are also disclosed; along with methods of controlling insects comprising applying said compositions to a locus where insects are present or are expected to be present.

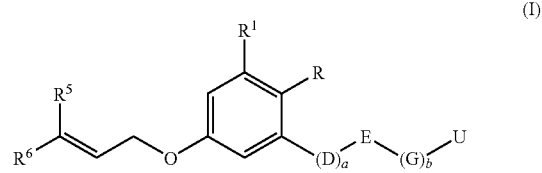

(I)

14 Claims, No Drawings

INSECTICIDAL 3-(DIHALOALKENYL) PHENYL DERIVATIVES

This application is a U.S. National Stage of International Application No. PCT/US2005/038226, filed Oct. 20, 2005, which claims the benefit of U.S. Provisional Application No. 60/621,380, filed Oct. 22, 2004.

FIELD OF THE INVENTION

The present invention relates to novel compounds and their use in controlling insects and acarids. In particular, it pertains to 3-(dihaloalkenyl)phenyl derivatives and agriculturally acceptable salts thereof, compositions containing them and methods for their use in controlling insects and acarids.

BACKGROUND OF THE INVENTION

It is well known that insects in general can cause significant damage, not only to crops grown in agriculture, but also, for example, to structures and turf where the damage is caused by soil-borne insects, such as termites and white grubs. Such damage may result in the loss of millions of dollars of value associated with a given crop, turf or structures. Insecticides and acaricides are useful for controlling insects and acarids which may otherwise cause significant damage to crops such as wheat, corn, soybeans, potatoes, and cotton to name a few. For crop protection, insecticides and acaricides are desired which can control the insects and acarids without damaging the crops, and which have no deleterious effects to mammals and other living organisms.

U.S. Pat. No. 5,922,880 discloses certain dihalopropene compounds for use as insecticides and acaricides of the general formula:

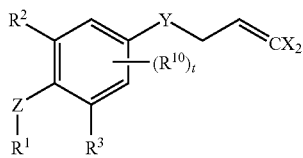

where Z is oxygen, sulfur, or $NR^4$ (wherein $R^4$ is hydrogen, or $C_1$-$C_3$ alkyl); Y is oxygen, sulfur, or NH; X's are independently chlorine or bromine; $R^2$, $R^3$, and $R^{10}$ are independently halogen, $C_1$-$C_3$ alkyl, or $C_1$-$C_3$ haloalkyl; t is an integer of 0 to 2; and $R^1$ is A—$(CR^5R^6)_p$CHR$^7$— (Q1), A-B—$(CR^5R^6)_p$CHR$^7$— (Q2), A—$(CR^{11}R^{12})_s$—B—$(CR^5R^6)_p$—CHR$^7$— (Q3), A-C($R^{13}$)=C($R^{14}$)—$(CR^5R^6)_p$—CHR$^7$— (Q4), A-B—$(CR^{11}R^{12})_s$—C($R^{13}$)=C($R^{14}$)—$(CR^5R^6)_p$—CHR$^7$— (Q5), A-B—$(CR^{11}R^{12})_s$—C(=O)—O—$(CR^5R^6)_p$—CHR$^7$— (Q6), or A-C($R^{13}$)=C($R^{14}$)—C(=O)—O—$(CR^5R^6)_p$—CHR$^7$— (Q7), where A is an optionally substituted heterocyclic ring; B is oxygen, S(O)$_q$, NR$^9$, C(=G$^1$)G$^2$ or G$^1$C(=G$^2$); q is an integer of 0 to 2; R$^9$ is hydrogen, acetyl or $C_1$-$C_3$ alkyl; G$^1$ and G$^2$ are independently oxygen and sulfur; R$^5$, R$^6$, R$^7$, R$^{11}$ and R$^{12}$ are independently selected from hydrogen, $C_1$-$C_3$ alkyl, or trifluoromethyl; R$^{13}$ and R$^{14}$ are independently selected from hydrogen, $C_1$-$C_3$ alkyl, halogen or trifluoromethyl; p is an integer of 0 to 6; and s is an integer of 1 to 6.

There is no disclosure or suggestion in the above-referenced patent of the 3-(dihaloalkenyl)phenyl structures and pesticidal activity of the compounds of the present invention.

SUMMARY OF THE INVENTION

In accordance with the present invention, it has now been found that certain novel 3-(dihaloalkenyl)phenyl derivatives are surprisingly active in the control of insects and acarids when used in the insecticidal and acaricidal compositions and methods of this invention. The novel derivatives are represented by the following general formula I:

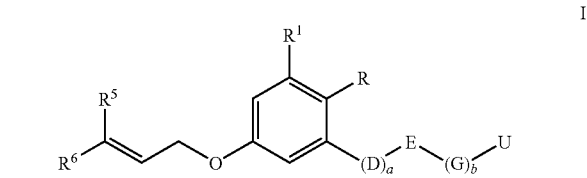

where
R and $R^1$ are independently selected from hydrogen, halogen, alkyl and cyano;
$R^5$ and $R^6$ are independently selected from bromine and chlorine;
a is an integer selected from 0 or 1;
and when a is 1,
D is —O—;
E is a bridging group

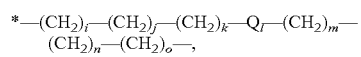

where
the asterisk denotes attachment at D; i, j, k, l, m, n and o are integers independently selected from 0 and 1;
and
when l is 1,
Q is a 5- or 6-membered heterocyclic ring containing from 1 to 4 nitrogen atoms and 0 to 1 oxygen or sulfur atom;
b is an integer selected from 0 or 1;
and, when b is 1,
G is selected from —O—, —CH$_2$O—, —CH=CH—, —S(O)$_h$—, —S(O)$_h$CH$_2$—, —S(O)$_h$C$_2$H$_4$—, —HC=N—, —C(=O)—, —OC(=O)—, —C(=O)O—, —C(=O)C$_2$H$_4$—, —C(=O)OCH$_2$—, —C(=O)NH—, —NR$^{14}$—, —N(oxide)R$^{14}$— and —NR$^{14}$C(=O)— where h is an integer selected from 0, 1 and 2 and R$^{14}$ is selected from hydrogen, alkyl, alkoxyalkyl, arylalkyl, alkenylalkyl, haloalkenylalkyl, dialkylphosphonate, alkylcarbonyl, haloalkylcarbonyl, alkoxyalkylcarbonyl, arylcarbonyl and alkylsulfonyl;
U is selected from the group consisting of:

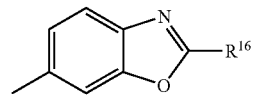

T,

-continued

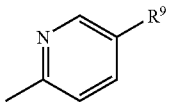

W,

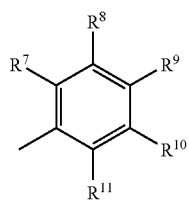

X,

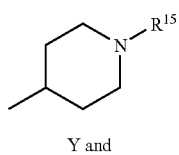

Y and

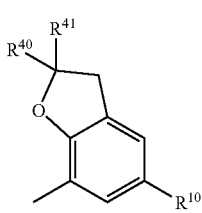

Z;

where;
R$^7$, R$^8$, R$^{10}$ and R$^{11}$ are independently selected from hydrogen and halogen;
R$^9$ is selected from hydrogen, halogen and haloalkyl;
R$^{15}$ is alkoxycarbonyl;
R$^{16}$ is selected from alkyl and haloalkyl;
R$^{40}$ and R$^{41}$ are independently selected from alkyl;
provided that when (a) R, R$^1$, R$^5$ and R$^6$ are chlorine; (b) a, i, j, k, n, and o are 0; (c) B$^1$ is —CH—; (d) m is 1 and (e) U is group X where R$^7$ through R$^{11}$ are hydrogen, then b is 1;
and
agriculturally acceptable salts thereof.

The present invention also includes compositions containing an insecticidally effective amount of at least one compound of formula I, and optionally, an effective amount of at least one additional compound, with at least one insecticidally compatible carrier.

The present invention also includes methods of controlling insects, in an area where control is desired, which comprise applying an insecticidally effective amount of the above composition to the locus of crops, or other areas where insects are present or are expected to be present.

The present invention also includes novel intermediates finding utility in the syntheses of compounds of formula I.

DETAILED DESCRIPTION OF THE INVENTION

The present invention relates to certain new and useful insecticidal and acaricidal compounds, namely 3-(dihaloalkenyl)phenyl derivatives (hereinafter termed "compounds of formula I") as depicted in general formula I:

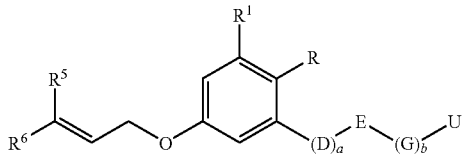

I where
R and R$^1$ are independently selected from hydrogen, halogen, alkyl and cyano;
R$^5$ and R$^6$ are independently selected from bromine and chlorine;
a is an integer selected from 0 or 1;
and when a is 1,
D is —O—;
E is a bridging group

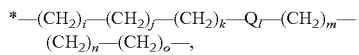

where
the asterisk denotes attachment at D; i, j, k, l, m, n and o are integers independently selected from 0 and 1;
and
when l is 1,
Q is a 5- or 6-membered heterocyclic ring containing from 1 to 4 nitrogen atoms and 0 to 1 oxygen or sulfur atom;
b is an integer selected from 0 or 1;
and, when b is 1,
G is selected from —O—, —CH$_2$O—, —CH═CH—, —S(O)$_h$—, —S(O)$_h$CH$_2$—, —S(O)$_h$C$_2$H$_4$—, —HC═N—, —C(═O)—, —OC(═O)—, —C(═O)O—, —C(═O)C$_2$H$_4$—, —C(═O)OCH$_2$—, —C(═O)NH—, —NR$^{14}$—, —N(oxide)R$^{14}$— and —NR$^{14}$C(═O)— where h is an integer selected from 0, 1 and 2 and R$^{14}$ is selected from hydrogen, alkyl, alkoxyalkyl, arylalkyl, alkenylalkyl, haloalkenylalkyl, dialkylphosphonate, alkylcarbonyl, haloalkylcarbonyl, alkoxyalkylcarbonyl, arylcarbonyl and alkylsulfonyl;
U is selected from the group consisting of:

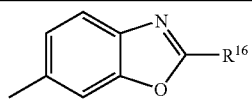

T,

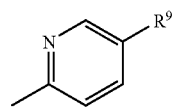

W,

-continued

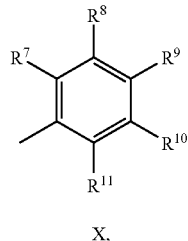

X,

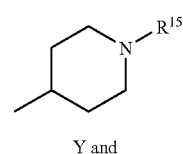

Y and

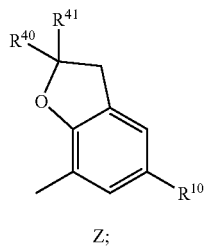

Z;

where;

$R^7$, $R^8$, $R^{10}$ and $R^{11}$ are independently selected from hydrogen and halogen;

$R^9$ is selected from hydrogen, halogen and haloalkyl;

$R^{15}$ is alkoxycarbonyl;

$R^{16}$ is selected from alkyl and haloalkyl;

$R^{40}$ and $R^{41}$ are independently selected from alkyl;

provided that when (a) R, $R^1$, $R^5$ and $R^6$ are chlorine; (b) a, i, j, k, n, and o are 0; (c) $B^1$ is —CH—; (d) m is 1 and (e) U is group X where $R^7$ through $R^{11}$ are hydrogen, then b is 1;

and agriculturally acceptable salts thereof.

Preferred 3-(dihaloalkenyl)phenyl derivatives from the group set forth above are those where Q is a cyclic moiety of the structure

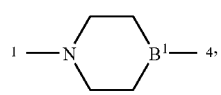

where, 1- and 4- denote points of attachment to the —$(CH_2)_k$— and to the —$(CH_2)_m$— sides of bridging group E; $B^1$ is —N— or —CH—;

or

Q is a cyclic moiety of the structure;

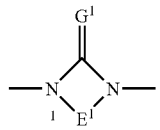

where $E^1$ is selected from —$CR^{34}$=$CR^{35}$—, *—$CR^{34}$=N—, *—N=$CR^{34}$—, —N=N—, *—C(=O)$CR^{34}$—, *—$CR^{34}$C(=O), —$CR^{34}R^{35}CR^{36}R^{37}$—, *—C(=O)$N^{34}$—, *—$NR^{34}$C(=O)—, *—S(O)$_s$$CR^{34}R^{35}$—, *—S(O)$_m$$NR^{34}$—, *—O$CR^{34}R^{35}$—, *—$CR^{34}R^{35}$O— and —C(=O)— where the asterisk denotes attachment to the nitrogen designated as 1 in Q, s is an integer selected from 0, 1 or 2, and $R^{34}$ through $R^{37}$, inclusively, are independently selected from hydrogen, halogen, alkyl, alkoxy, alkoxyalkyl, haloalkyl, alkoxycarbonyl, nitro, cyano, amino, alkylamino and aryl; and $R^{34}$ through $R^{37}$ in geminal positions may be taken together to form 5-, 6- or 7-membered spiro rings comprised of carbon, nitrogen and oxygen, or $R^{34}$ through $R^{37}$ in adjacent positions may be taken together to form 5-, 6- or 7-membered rings comprised of carbon, nitrogen and oxygen or a benzo-fused ring;

$G^1$ is selected from O, S, N-$J^1$, or C-$J^1$, where $J^1$ is cyano or nitro;

More preferred 3-(dihaloalkenyl)phenyl derivatives from the group set forth above are those where R and $R^1$ are independently selected from halogen; $R^5$ and $R^6$ are each chlorine; a and b are 0;

E is a bridging group

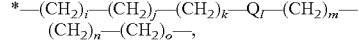

where the asterisk denotes attachment at D;

i, j, k m, n and o are each 0;

l is 1 and Q is a cyclic moiety of the structure

where, 1- and 4- denote points of attachment to the —$(CH_2)_k$— and to the —$(CH_2)_m$— sides of bridging group E; $B^1$ is —N—; and U is W and $R^9$ is haloalkyl.

Other preferred 3-(dihaloalkenyl)phenyl derivatives of the group set forth above are those where R and $R^1$ are independently selected from halogen; $R^5$ and $R^6$ are each chlorine;

E is a bridging group

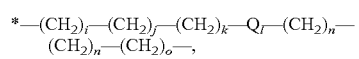

where the asterisk denotes attachment at D;

a, i, j, k m, n and o are each 0;

l is 1 and Q is a cyclic moiety of the structure;

where,
1- and 4- denote points of attachment to the —$(CH_2)_k$— and to the —$(CH_2)_n$— sides of bridging group E; $B^1$ is —N—;
b is 1, G is selected from —C(=O)OCH$_2$—, —C(=O)—, —C(=O)CH$_2$—, —C(=O)C$_2$H$_4$— or —SO$_2$C$_2$H$_4$—;
U is X; $R^8$, $R^{10}$ and $R^{11}$ are hydrogen.

Still other preferred 3-(dihaloalkenyl)phenyl derivatives of the group set forth above are those where R and $R^1$ are independently selected from hydrogen and halogen; $R^5$ and $R^6$ are each chlorine;
a and b are each 1 and G is —O—;
E is a bridging group

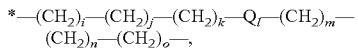

where the asterisk denotes attachment at D;
l and o are each 0, i, j, k are each 1 and m and n are selected from 0 or 1,
and
U is Z.

Additional preferred 3-(dihaloalkenyl)phenyl derivatives of the group set forth above are those where R and $R^1$ are independently selected from halogen; $R^5$ and $R^6$ are each chlorine;
a and b are each 1 and G is —O—;
E is a bridging group

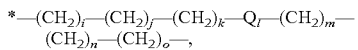

where the asterisk denotes attachment at D;
l is 0, i, j and k are each 1 and m, n and o are independently selected from 0 or 1,
and
U is g X; $R^7$, $R^8$, $R^{10}$ and $R^{11}$ are each hydrogen and $R^9$ is halogen.

Additional preferred 3-(dihaloalkenyl)phenyl derivatives of the group set forth above are those where R and $R^1$ are independently selected from halogen; $R^5$ and $R^6$ are each chlorine;
E is a bridging group

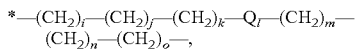

where the asterisk denotes attachment at D;
a, i, j, k m, n and o are each 0;
l is 1 and Q is a cyclic moiety of the structure

where $B^1$ is —CH—;
b is 1 and G is —CH$_2$O—;
U is W and $R^9$ is haloalkyl.

Additional preferred 3-(dihaloalkenyl)phenyl derivatives of the group set forth above are those where R and $R^1$ are independently selected from halogen; $R^5$ and $R^6$ are each chlorine;
a is 1;
E is a bridging group

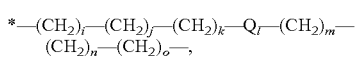

where the asterisk denotes attachment at D;
i and j are each 1 and k, l, m and o are 0;
b is 0;
and
U is Y.

Further preferred 3-(dihaloalkenyl)phenyl derivatives from the group set forth above are those where R and $R^1$ are selected from halogen; $R^5$ and $R^6$ are each chlorine;
a and b are 0;
E is a bridging group

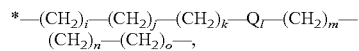

where the asterisk denotes attachment at D;
i, j, k m, n and o are each 0;
l is 1 and Q is a cyclic moiety of the structure

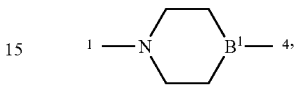

where,
1- and 4- denote points of attachment to the —$(CH_2)_k$— and to the —$(CH_2)_m$— sides of bridging group E; $B^1$ is —N—;
and
U is X; $R^7$, $R^8$, $R^{10}$ and $R^{11}$ are each hydrogen and $R^9$ is haloalkyl.

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties. The compounds of the present invention may also exist as tautomers, in which migration of a hydrogen atom within the molecule results in two or more structures, which are in equilibrium. The compounds of the present invention may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention comprise causing an insecticidally effective amount of a compound of formula I to be administered to insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which are referred to as pro-insecticides.

Another aspect of the present invention relates to compositions containing an insecticidally effective amount of at least one compound of formula I.

Another aspect of the present invention relates to compositions containing an insecticidally effective amount of at least one compound of formula I, and an effective amount of at least one additional compound.

Another aspect of the present invention relates to methods of controlling insects by applying an insecticidally effective amount of a composition as set forth above to a locus of crops such as, without limitation, cereals, cotton, vegetables, and fruits, or other areas where insects are present or are expected to be present.

Another aspect of the present invention relates to novel intermediates finding utility in the syntheses of compounds of formula I.

The present invention also includes the use of the compounds and compositions set forth herein for control of nonagricultural insect species, for example, dry wood termites and subterranean termites; as well as for use as pharmaceutical agents. In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* spp., *Rhodnius* spp., *Ctenocephalides canis*, and other species.

As used in this specification and unless otherwise indicated the substituent terms "alkyl" and "alkoxy", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The term "alkenyl" and "alkynyl" used alone or as part of a larger moiety, includes straight or branched chains of at least two carbon atoms containing at least one carbon-carbon double bond or triple bond, and preferably up to 12 carbon atoms, more preferably up to ten carbon atoms, most preferably up to seven carbon atoms. The term "aryl" refers to an aromatic ring structure, including fused rings, having six to ten carbon atoms, for example, phenyl or naphthyl. The term "heteroaryl" refers to an aromatic ring structure, including fused rings, in which at least one of the atoms is other than carbon, for example, without limitation, sulfur, oxygen, or nitrogen. The term "DMF" refers to N,N-dimethylformamide. The term "THF" refers to tetrahydrofuran. The term "DMPU" refers to 1,3-dimethyl-3,4,5,6-tetrahydro-2 (1H)-pyrimidinone. The term "halogen" or "halo" refers to fluorine, bromine, iodine, or chlorine. The term "ambient temperature" or "room temperature" often abbreviated as "RT", for example, in reference to a chemical reaction mixture temperature, refers to a temperature in the range of 20° C. to 30° C. The term "insecticidal" or "acaricidal", "insecticide" or "acaricide" refers to a compound of the present invention, either alone or in admixture with at least one of an additional compound, or with at least one compatible carrier, which causes the destruction or the inhibition of action of insects or acarids. The term "independently selected from" as set forth above and in the claims section of the present specification refers to the possibility that moieties, for example the $R^5$ and $R^6$, may be the same or they may be different within the group that the selection is made.

The 3-(dihaloalkenyl)phenyl derivatives of formula I can be synthesized by methods that are individually known to one skilled in the art from available intermediate compounds.

Scheme 1 below illustrates a general procedure for synthesizing 3-(dihaloalkenyl)phenyl derivatives of formula I, inter alia, where a, b, i, j, k, m, n and o are each 0; l is 1 and Q is a cyclic moiety of the structure

where 1- and 4- denote points of attachment to the —$(CH_2)_k$— and to the —$(CH_2)_m$— sides of bridging group E and $B^1$ is —N—:

Scheme 1

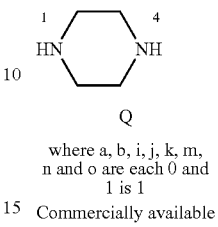

Q where a, b, i, j, k, m, n and o are each 0 and l is 1
Commercially available where U is W and $R^9$ is $CF_3$
Commercially available

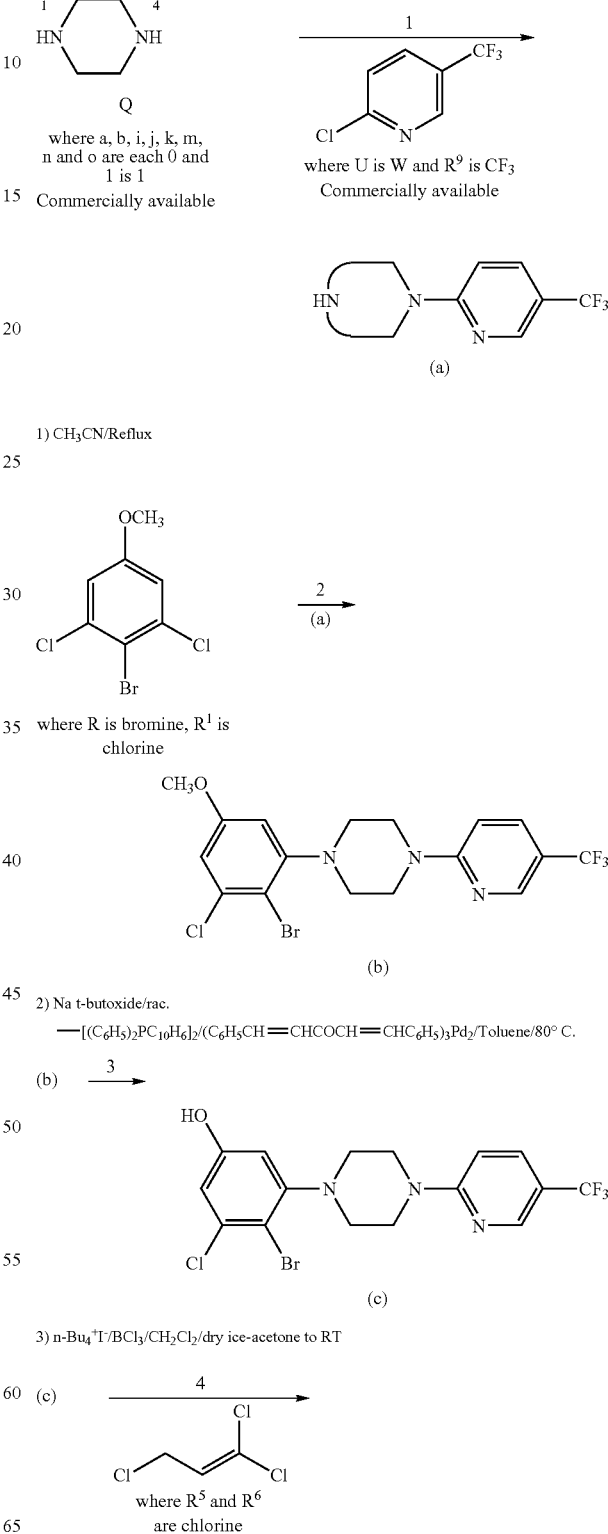

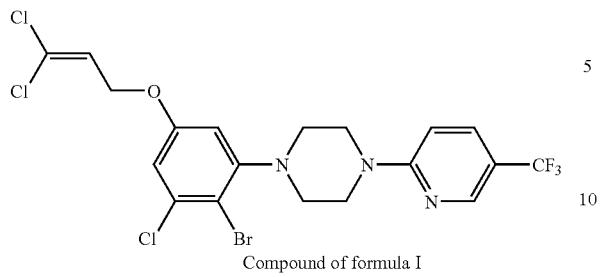

Compound of formula I

4) K$_2$CO$_3$/DMF/65° C.

As depicted in Scheme 1, piperazine (Moiety Q) was reacted with an appropriately substituted halo derivative, such as 2-chloro-5-(trifluoromethyl)pyridine (where U is W and R$^9$ is CF$_3$), affording the corresponding intermediate (a). Intermediate (a) was in turn reacted with an appropriate halo-substituted alkoxybenzene derivative, for example 2-bromo-1,3-dichloro-5-methoxybenzene (where R is bromine and R$^1$ is chlorine), yielding intermediate (b). Intermediate (b), for example, 2-bromo-3-chloro-5-methoxy-1-{4-[5-(trifluoromethyl)(2-pyridyl)]piperazinyl}benzene, was then reduced with, for example, boron trichloride, affording the corresponding phenol, intermediate (c). Intermediate (c) was then reacted under basic conditions with an appropriate haloalkene derivative (where R$^5$ and R$^6$ is chlorine), thereby providing a compound of formula I. Example 1, set forth below, provides a detailed method by which a compound of formula I of this type is made.

Scheme 2 below illustrates a general procedure for synthesizing 3-(dihaloalkenyl)phenyl derivatives of formula I, inter alia, where l, n and o) are each 0 and i, j, k and m are each 1; U is group Z where R$^{40}$ and R$^{41}$ are each methyl:

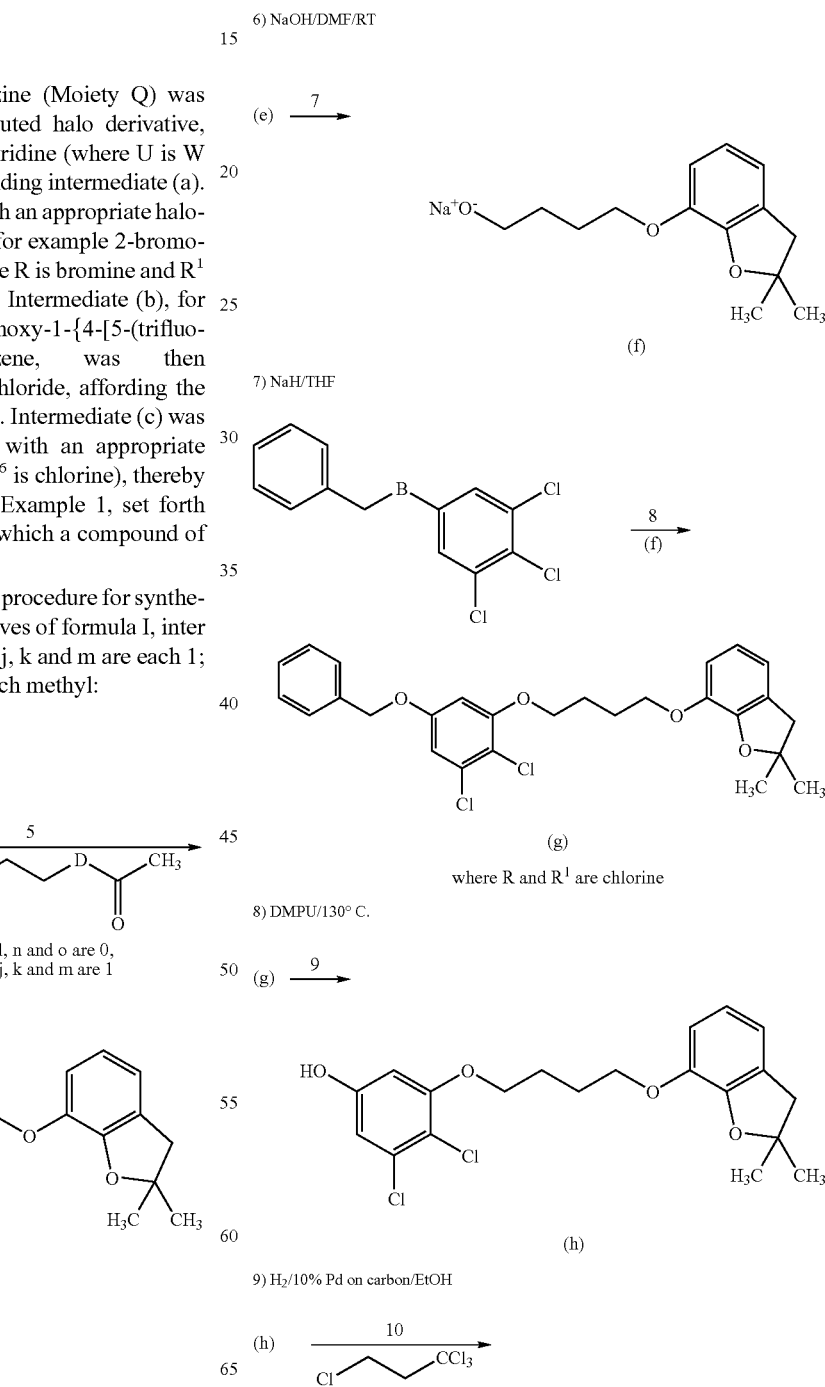

-continued

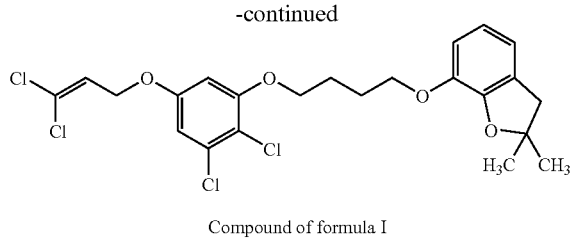

Compound of formula I

10) K$_2$CO$_3$/DMF/80° C.

As depicted in Scheme 2, an appropriately substituted benzofuran-7-ol (where U is group W; R$^{40}$ and R$^{41}$ are CH$_3$ and G is —O—), for example 7-hydroxybenzofuran, was reacted with a haloalkyl acetate of appropriate chain length (for example, where l is 0; a, b, i, j, k and m are 1; G is —O—), affording the corresponding benzofuran-7-ylalkyl acetate, Intermediate (d). Intermediate (d) was then reduced with strong base, yielding the corresponding alcohol, for example 4-(2,2-dimethyl-2,3-dihydrobenzo[2,3-b]furan-7-yloxy)butan-1-ol, Intermediate (e). Intermediate (e) was then converted to its sodium salt (f), which was in turn reacted with an appropriate (arylalkyloxy substituted)halobenzene, for example 1,2,3-trichloro-5-(phenylmethoxy)benzene (where R and R$^1$ are chlorine), providing the corresponding phenoxyalkylbenzofuran-7-yloxy derivative, intermediate (g). Intermediate (g) was then reduced under hydrogenation conditions, yielding the corresponding phenol, intermediate (h), for example 3-[4-(2,2-dimethyl(2,3-dihydrobenzo[2,3-b]furan-7-yloxy))butoxy]4,5-dichlorophenol. Intermediate (h) was then reacted under basic conditions with an appropriate tetrahaloalkane derivative (where R$^5$ and R$^6$ are chlorine), thereby providing a compound of formula I. Example 2, set forth below, provides a detailed method by which a compound of formula I of this type is made.

One skilled in the art will, of course, recognize that the formulation and mode of application of a toxicant may affect the activity of the material in a given application. Thus, for agricultural use the present insecticidal compounds may be formulated as a granule of relatively large particle size (for example, 8/16 or 4/8 US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselgubr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (Ecs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvents. For insecticidal applications these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to Ecs, except that the active ingredient is suspended in a liquid carrier, generally water. Flowables, like Ecs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal compounds of this invention may be formulated and/or applied with one or more additional compounds. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Additional compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with one or more additional compound, e.g., with other pesticides such as herbicides, the herbicides include, without limitation, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)2-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide ("achlorsulfuron"), 2-[[[[[(4,6-dimethoxy-2-pyrimidinyl)amino]carbonyl]amino]ydroxid]methyl]benzoic acid ("bensulfuron"), 2-[[[[(4,6-dimethoxy-2-pyrimidinyl)amino]carbonyl]amino]sulfonyl]-1-methyl-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N [[(4-methoxy-6-methyl-1,3,5-triazin-2-yl)amino]carbonyl] benzenesulfonamide ("triasulfuron"); 2-(4-aryloxyphenoxy)alkanoic acids such as (+/−)-2[4-[(6-chloro-2-benzoxazolyl)oxy]phenoxy]-propanoic acid (fenoxaprop"), (+/−)-2-[4[[5-(trifluoromethyl)-2-pyridinyl]oxy]-phenoxy] propanoic acid ("fluazifop"), (+/−)-2-[4-(6chloro-2-quinoxalinyl)oxy]-phenoxy]propanoic acid ("quizalofop"), and (+/−)-2-[(2,4-dichlorophenoxy)phenoxy]propanoic acid ("diclofop"); benzothiadiazinones such as 3-(1-methylethyl)-1H-1,2,3-benzothiadiazin-4(3H)-one-2,2-dioxide ("bentazone"); 2-chloroacetanilides such as N-(butoxymethyl)-2-chloro-N-(2,6-diethylphenyl)acetamide ("butachlor"), 2-chloro-N-(2-ethyl-6-methylphenyl)-N-(2-methoxy-1-methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl)acetamide ("dimethenamide"); arenecarboxylic acids such as 3,6-dichloro-2-methoxybenzoic acid ("dicamba"); pyridyloxyacetic acids such as [(4-amino-3,5-dichloro-6-fluoro-2-pyridinyl)oxy]acetic acid ("fluoroxypyr")"); aryl triazolinones such as 1H-1,2,4-triazol-1-carboxamide ("amicarbazone"), 1,2,4-triazolo[4,3-a]pyridine-3(2H)-one ("azafenidin"), N-(2,4-dichloro-5-[4-(difluoromentyl)-4,5-dihydro-3-methyl-5-oxo-1H-1,2,4-triazol-1-yl]phenyl)methanesulfonamide ("sulfentrazone") and ethyl α,2-dichloro-5-[4-(difluoromethyl)-4,5-dihydro-3-methyl-5-oxo-1H-1,2,4-triazol-1-yl]-4-fluorobenzenepropanoate ("carfentrazone-ethyl"); isoxazolidinones such as 2[(2-chlorophenyl)methyl]-4,4-dimethyl-3-isoxazoline ("clomazone"); and other herbicides.

When the active insecticidal compounds of the present invention are used in combination with one or more of second compound, e.g., with other pesticides such as other insecticides, the other insecticides include, for example: organophosphate insecticides, such as chlorpyrifos, diazinon, dimethoate, malathion, parathion-methyl, and terbufos; pyrethroid and non-pyrethroid insecticides, such as as fenvalerate, deltamethrin, fenpropathrin, cyfluthrin, flucythrinate, cypermethrin, alpha-cypermethrin, beta-cypermethrin, zeta-cypermethrin, bifenthrin, resolved cyhalothrin, etofenprox, esfenvalerate, tralomethrin, tefluthrin, cycloprothrin, betacyfluthrin, silafluofen, and acrinathrin; carbamate insecticides, such as ydroxid, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, noviflumuron, flufenoxuron, and lufenuron; and other insecticides, such as, without limitation, amitraz, clofentezine, fenpyroximate, hexythiazox, cyhexatin, spinosad, imidacloprid, chlorfenaptr, hydramethylon, acequinocyl, fenbutatin-oxide, methoxyfenozide, tebufenozide, halofenozide, indoxacarb, ydroxid, ethiprole, etoxazole, bifenazate, spirodiclofen, spiromesifen, methoprene, pyriproxyfen, fenoxycarb, pymetrozine, abamectin, emamectin benzoate, milbemectin, and other insecticides.

When the active insecticidal compounds of the present invention are used in combination with one or more additional compound, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, iprodione, captan, dinocap, do dine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with one or more additional compound, e.g., with other pesticides such as nematicides, the nematicides include, for example: carbofuran, carbosulfan, ydroxid, ydroxid, ethoprop, fenamphos, oxamyl, isazofos, cadusafos, and other nematicides.

When the active insecticidal compounds of the present invention are used in combination with one or more additional compound, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more additional compound, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne *cyanobacteria*.

Fertilizers are plant food supplements, which commonly contain nitrogen, phosphorus, and potassium. When the active insecticidal compounds of the present invention are used in combination with one or more additional compound, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

Example 1

This example illustrates one protocol for the preparation of 5-(3,3-dichloroprop-2-enyloxy)-2-bromo-3-chloro-1-{4-[5-(trifluoromethyl)(2-pyridyl)]piperazinyl}-benzene Compound 19

Step A Synthesis of
2-bromo-1,3-dichloro-5-methoxybenzene as an intermediate

A solution of 5.0 grams (0.028 mole) of 1,3-dichloro-5-methoxybenzene (commercially available) in 35 mL of acetone was stirred and 5.0 grams (0.028 mole) of N-bromosuccinimide, then one mL of aqueous 10% hydrochloric acid were added. Upon completion of additions the reaction mixture was stirred at ambient temperature during a 30-minute period. After this time the reaction mixture was concentrated under reduced pressure to a residue. The residue was slurried in 20 mL of hexane and an insoluble material was removed by filtration. The filtrate was concentrated under reduced pressure, yielding 4.8 grams of the subject compound. The NMR spectrum was consistent with the proposed structure.

Step B Synthesis of
[5-(trifluoromethyl)-2-pyridylpiperazine as an intermediate

A stirred solution of 7.1 grams (0.083 mole) of piperazine (commercially available) and 5.0 grams (0.028 mole) of 2-chloro-5-(trifluoromethyl)pyridine (commercially available) in 75 mL of acetonitrile was heated at reflux during a two-hour period. After this time the reaction mixture was allowed to cool to ambient temperature, and then it was filtered. The filtrate was concentrated under reduced pressure to a residue. The residue was dissolved in 75 mL of methylene chloride and washed with two 50 mL portions of water. The organic layer was dried with sodium sulfate, filtered, and the filtrate was concentrated under reduced pressure to a residue. The residue was purified with column chromatography on silica gel using 100% methylene chloride, then 5% methanol in methylene chloride as eluants. The appropriate fractions were combined and concentrated under reduced pressure, yielding 4.5 grams of the subject compound. The NMR spectrum was consistent with the proposed structure.

Step C Synthesis of a mixture of 2-bromo-3-chloro-5-methoxy-1-{4-[5-(trifluoromethyl)(2-pyridyl)]piperazinyl}benzene and 1,3-dichloro-5-methoxy-2-{4-[5-(trifluoromethyl)(2-pyridyl)]piperazinyl}benzene as intermediates A stirred mixture of 3.0 grams (0.012 mole) of 2-bromo-1,3-dichloro-5-methoxybenzene (Step A), 2.7 grams (0.012 mole) of [5-(trifluoromethyl)-2-pyridylpiperazine (Step B), 0.02 gram (0.00024 mole) of tris(ydroxide eneacetone)dipalladium (0), 0.45 gram (0.00072 mole) of ydroxi-2,2'bis(diphenylphosphino)-1,1'-binaphthyl and 2.1 grains (0.022 mole) of sodium tert-butoxide in 150 mL of toluene was warmed to 80° C. where it was maintained during a 24-hour period. After this time the reaction mixture was cooled and poured into 250 mL of water. The organic layer was separated, and the aqueous layer was extracted with two 75 mL portions of diethyl ether. The organic layer and the extracts were combined and washed with 50 mL of an aqueous solution saturated with sodium chloride. The organic layer-extract combination was dried with sodium sulfate, filtered, and the filtrate was concentrated under reduced pressure to a residue. The residue, which was a mixture of products, was separated into its components by column chromatography on silica gel using 25% methylene chloride in hexane, then 50% methylene chloride in hexane as eluants. Appropriate fractions were combined and concentrated under reduced pressure, yielding 1.8 grams of 1,3-dichloro-5-methoxy-2-{4-[5-(trifluoromethyl)(2-pyridyl)]piperazinyl}benzene, and other appropriate fractions were combined and concentrated under reduced pressure, yielding 0.45 gram of 2-bromo-3-chloro-5-methoxy-1-{4-[5-(trifluoromethyl)(2-pyridyl)] piperazinyl}benzene. The NMR spectra of both compounds were consistent with the proposed structures.

Step D Synthesis of 4-bromo-5-chloro-3-{4-[5-(trifluoromethyl)(2-pyridyl)]piperazinyl)phenol as an intermediate A stirred solution of 0.38 gram (0.00084 mole) of 2-bromo-3-chloro-5-methoxy-1-{4-[5-(trifluoromethyl)(2-pyridyl)]piperazinyl}benzene and 0.78 gram (0.0021 mole) of n-tetrabutylammonium iodide in 30 mL of methylene chloride was cooled in a dry-ice/acetone bath and 2.1 mL (0.0021 mole, a 1.0M solution in methylene chloride) of boron trichloride was added dropwise. Upon completion of addition the reaction mixture was kept cold in the dry-ice/acetone bath for an additional 30-minute period, then it was allowed to warm to ambient temperature where it stirred during a three-hour period. After this time the reaction mixture was cooled in an ice/water bath and 15 mL of water was added. The organic layer was separated and the aqueous layer was extracted with one 15 mL portion of methylene chloride. The organic layer and the extract were combined and dried with sodium sulfate. The mixture was filtered, and the filtrate was concentrated under reduced pressure to a residue. The residue was purified with column chromatography on silica gel using as eluants: 50% hexane in methylene chloride, then 100% methylene chloride, and finally 2% methanol in methylene chloride. The appropriate fractions were combined and concentrated under reduced pressure, yielding 0.17 gram of the subject compound. The NMR spectrum was consistent with the proposed structure.

Step E Synthesis of Compound 19

In a vial were placed 0.13 gram (0.0003 mole) of 4-bromo-5-chloro-3-{4-[5-(trifluoromethyl)(2-pyridyl)]piperazinyl} phenol, 0.09 gram (0.0006 mole) of 1,1,3-trichloropropene, 0.083 gram (0.006 mole) of potassium carbonate and 6 mL of DMF. The vial was then sealed and, with agitation, it was warmed to 65° C., where it was maintained during an 18-hour period. After this time the vial was cooled and the contents were poured into 25 mL of water. The mixture was extracted with two 15 mL portions of diethyl ether. The combined extracts were dried with sodium sulfate, filtered, and the filtrate was concentrated under reduced pressure to a residue. The residue was purified with column chromatography on silica gel using 50% hexane in methylene chloride as an eluant. The appropriate fractions were combined and concentrated under reduced pressure, yielding 0.12 gram of Compound 19. The NMR spectrum was consistent with the proposed structure.

Example 2

This example illustrates one protocol for the preparation of 7-{4-[5-(3,3-dichloroprop-2-enyloxy)-2,3-dichlorophenoxy]butoxy}-2,2-dimethyl-2,3-dihydro-benzo[b]furan Compound 2

Step A Synthesis of 4-(2,2-dimethyl-2,3-dihydrobenzo[2,3-b]furan-7-yloxy)butyl acetate as an intermediate Under a nitrogen atmosphere a solution of 5.0 grams (0.030 mole) of 7-hydroxybenzofuran (known compound), 6.5 grams (0.033 mole) of 4-bromobutyl acetate and 6.2 grams (0.045 mole) of potassium carbonate in 75 mL of DMF was stirred at ambient temperature during a five-day period. The reaction mixture was then stirred with 75 mL of water and saturated with solid sodium chloride. The mixture was extracted with three 50 mL portions of diethyl ether, and the combined extracts were washed with one 50 mL portion of water. The organic layer was then dried with sodium sulfate, filtered, and the filtrate was concentrated under reduced pressure, yielding 8.0 grams of the subject compound. The NMR spectrum was consistent with the proposed structure.

Step B Synthesis of 4-(2,2-dimethyl-2,3-dihydrobenzo[2,3-b]furan-7-yloxy)butan-1-ol as an intermediate With stirring, a solution of 2.24 grams (0.056 mole) of sodium ydroxide in 125 mL of methanol was added 8.0 grams (0.028 mole) of 4-(2,2-dimethyl-2,3-dihydrobenzo[2,3-b]furan-7-yloxy)butyl acetate. Upon completion of addition the reaction mixture was stirred at ambient temperature during a three-hour period. After this time 150 mL of water was added to the reaction mixture, and the mixture was acidified to a pH of 6 with concentrated hydrochloric acid. The mixture was then extracted with four 50 mL portions of diethyl ether. The combined extracts were washed with one 50 mL portion of water, dried with sodium sulfate, filtered, and the filtrate was concentrated under reduced pressure, yielding 5.6 grams of the subject compound. The NMR spectrum was consistent with the proposed structure.

Step C Synthesis of 1,2,3-trichloro-5-(phenylmethoxy)benzene as an intermediate

A stirred solution of 5.8 grams (0.029 mmole) of 3,4,5-trichlorophenol (commercially available), 3.8 mL (0.032 mole) of benzyl bromide and 4.45 grams (0.032 mole) of potassium carbonate in 75 mL of DMF was warmed to 80° C. where it was maintained during a two-hour period. After this time the reaction mixture was allowed to cool to ambient temperature and then 150 mL of water was added. The mixture was extracted with three 50 mL portions of diethyl ether and the combined extracts were washed with one 50 mL portion of water. The organic layer was dried with sodium sulfate, filtered, and the filtrate was concentrated under reduced pressure, yielding 7.1 grams of the subject compound. The NMR spectrum was consistent with the proposed structure.

Step D Synthesis of 7-{4-[2,3-dichloro-5-(phenylmethoxy)phenoxy}-2,2-dimethyl-2,3-dihydrobenzo [b]furan as an intermediate Under a nitrogen atmosphere, a solution of 0.32 gram (0.008 mole) of 60% sodium hydride (in mineral oil) in 2 mL of THF was stirred and a solution of 1.65 grams (0.007 mole) of 4-(2,2-dimethyl-2,3-dihydrobenzo[2,3-b]furan-7-yloxy) butan-1-ol (Step B) in 10 mL of THF was added drop-wise.

Upon completion of addition the reaction mixture was warmed to 40° C. where it stirred during a 15-minute period. After this time the reaction mixture was allowed to cool to ambient temperature and then it was concentrated under reduced pressure to a residue. To the residue was added a solution of 1.00 gram (0.0035 mole) of 1,2,3-trichloro-5-(phenylmethoxy)benzene (Step C) in 35 mL of 1,3-dimethyl-3,4,5,6-tetrahydro-2(1H)-pyrimidinone. Upon completion of addition the reaction mixture was heated to 130° C. where it was stirred during an 18-hour period. After this time the reaction mixture was cooled and stirred with 50 mL of an aqueous solution saturated with sodium chloride, then it was extracted with three 25 mL portions of diethyl ether. The combined extracts were washed with one 25 mL portion of water, dried with sodium sulfate, filtered, and the filtrate was concentrated under reduced pressure to a residue. The residue was purified with column chromatography on silica gel using 25% methylene chloride in hexane and 50% methylene chloride in hexane as eluants. The appropriate fractions were combined and concentrated under reduced pressure, yielding 0.54 gram of the subject compound. The NMR spectrum was consistent with the proposed structure.

Step E Synthesis of 3-[4-(2,2-dimethyl(2,3-dihydrobenzo[2,3-b]furan-7-yloxy))butoxy]-4,5-dichlorophenol as an intermediate A mixture of 0.5 gram (0.001 mole) of 7-{4-[2,3-dichloro-5-(phenylmethoxy)phenoxy}-2,2-dimethyl-2,3-dihydrobenzo[b]furan and 0.1 gram (catalyst) of 10% palladium on carbon in 75 mL of ethanol was placed in a Parr hydrogenation bottle and hydrogenated using a Parr hydrogenation apparatus. Upon the theoretical uptake of hydrogen gas, the reaction mixture was filtered to remove the catalyst, and the filtrate was concentrated under reduced pressure to a residue. The residue was purified with column chromatography on silica gel using 100% methylene chloride, then 5% methanol in methylene chloride as eluants. The appropriate fractions were combined and concentrated under reduced pressure, yielding 0.17 gram of the subject compound. The NMR spectrum was consistent with the proposed structure.

Step F Synthesis of Compound 2

A stirred solution of 0.17 gram (0.00043 mole) of 3-[4-(2,2-dimethyl(2,3-dihydrobenzo[2,3-b]furan-7-yloxy))butoxy]-4,5-dichlorophenol, 0.12 gram (0.00064 mole) of 1,1,1,3-tetrachloropropane and 0.12 gram (0.00086 mole) of potassium carbonate in 20 mL of DMF was warmed to 80° C. where it was maintained during an 18-hour period. After this time the reaction mixture was cooled to ambient temperature and 25 mL of an aqueous solution saturated with sodium chloride was added. The mixture was then extracted with two 25 mL portions of diethyl ether. The combined extracts were washed with one 25 mL portion of water, dried with sodium sulfate, filtered, and the filtrate was concentrated under reduced pressure to a residue, yielding 0.23 gram of Compound 2. The NMR spectrum was consistent with the proposed structure.

The following table sets forth some compounds of formula I:

TABLE 1

Insecticidal 3-(Dihaloalkenyl)phenyl Derivatives

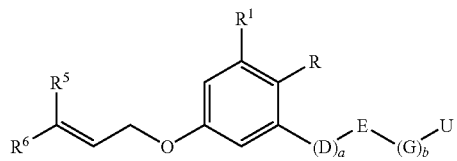

I where $R^5$ and $R^6$ are chlorine; a and b are each 1; G is —O—; E is the bridging group
*—(CH$_2$)$_i$—(CH$_2$)$_j$—(CH$_2$)$_k$—Q$_l$—(CH$_2$)$_m$—(CH$_2$)$_n$—(CH$_2$)$_o$—,
where i, j, and k are 1; m and n are 0 or 1; l and o are 0; U is Z:

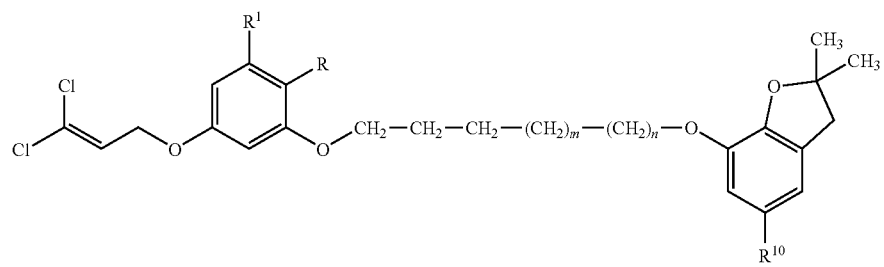

I-1

| Cmpd. No. | R | $R^1$ | m | n | $R^{10}$ |
|---|---|---|---|---|---|
| 1 | H | H | 0 | 0 | Cl |
| 2 | Cl | Cl | 1 | 0 | H |
| 3 | H | H | 1 | 0 | Cl |

TABLE 1-continued

Insecticidal 3-(Dihaloalkenyl)phenyl Derivatives

| 4 | Cl | Cl | 1 | 1 | H  |
| 5 | Cl | H  | 0 | 0 | Cl | where $R^5$ and $R^6$ are chlorine; a and b are each 1, G is —O—; E is the bridging group
*—(CH$_2$)$_i$—(CH$_2$)$_j$—(CH$_2$)$_k$—Q$_l$—(CH$_2$)$_m$—(CH$_2$)$_n$—(CH$_2$)$_o$—,
where i, j, and k are 1; m, n and o are 0 or 1; l is 0; U is X; $R^7$, $R^8$, $R^{10}$ and $R^{11}$ are hydrogen:

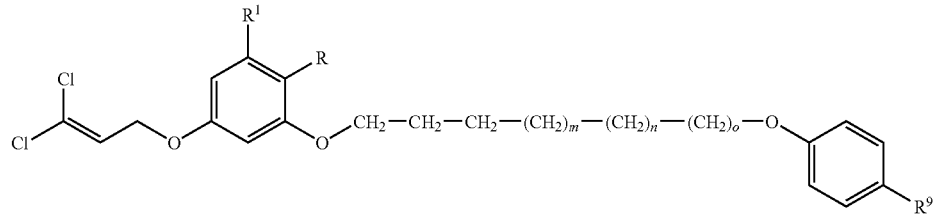

I-2

| Cmpd. No. | R  | $R^1$ | m | n | o | $R^9$ |
|-----------|----|-------|---|---|---|-------|
| 6         | Cl | Cl    | 1 | 0 | 0 | Cl    |
| 7         | Cl | Cl    | 0 | 0 | 0 | Cl    |
| 8         | Cl | Cl    | 1 | 1 | 0 | Cl    |
| 9         | Cl | Cl    | 1 | 1 | 1 | Cl    | where $R^5$ and $R^6$ are chlorine; a is 0 and b is 0 or 1; E is the bridging group
*—(CH$_2$)$_i$—(CH$_2$)$_j$—(CH$_2$)$_k$—Q$_l$—(CH$_2$)$_m$—(CH$_2$)$_n$—(CH$_2$)$_o$—,
where i, j, k, m, n and o are 0; l is 1; Q is the cyclic moiety

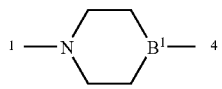

where $B^1$ is —N—; U is X; $R^8$, $R^{10}$ and $R^{11}$ are hydrogen:

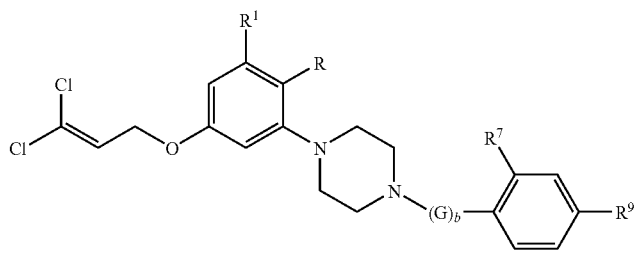

I-3

| Cmpd. No. | R  | $R^1$ | b | G          | $R^7$ | $R^9$ |
|-----------|----|-------|---|------------|-------|-------|
| 10        | Cl | Cl    | 1 | C(=O)      | H     | CF$_3$|
| 11        | Cl | Cl    | 1 | C(=O)OCH$_2$ | Cl  | H     |
| 12        | Cl | Cl    | 1 | C(=O)C$_2$H$_4$ | H | H     |
| 13        | Cl | Cl    | 0 | —          | H     | CF$_3$|
| 14        | Cl | Cl    | 1 | C(=O)CH$_2$ | H    | H     |
| 15        | Cl | Cl    | 1 | C(=O)CH$_2$ | H    | Cl    |
| 16        | Cl | Cl    | 1 | SO$_2$C$_2$H$_4$ | H | Cl    |

TABLE 1-continued

Insecticidal 3-(Dihaloalkenyl)phenyl Derivatives where $R^5$ and $R^6$ are chlorine; a is 0; b is 0 or 1; E is the bridging group
*—(CH$_2$)$_i$—(CH$_2$)$_j$—(CH$_2$)$_k$—Q$_l$—(CH$_2$)$_m$—(CH$_2$)$_n$—(CH$_2$)$_o$—,
where i, j, k, m, n and o are 0; l is 1; Q is the cyclic moiety

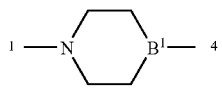

where $B^1$ is —N—; U is W:

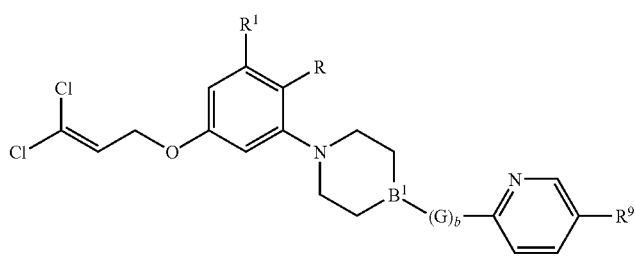

I-4

| Cmpd. No. | R | R$^1$ | B$^1$ | b | G | R$^9$ |
|---|---|---|---|---|---|---|
| 17 | Cl | Cl | N | 0 | — | CF$_3$ |
| 18 | Br | Cl | CH | 1 | CH$_2$O | CF$_3$ |
| 19 | Br | Cl | N | 0 | — | CF$_3$ | where $R^5$ and $R^6$ are chlorine; a is 1; b is 0; E is the bridging group
*—(CH$_2$)$_i$—(CH$_2$)$_j$—(CH$_2$)$_k$—Q$_l$—(CH$_2$)$_m$—(CH$_2$)$_n$—(CH$_2$)$_o$—,
where i and j are 1; k, l, m, n and o are 0; U is Y:

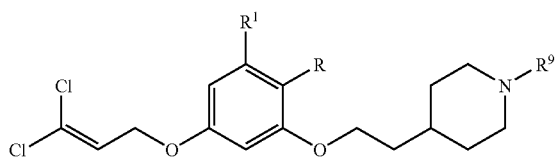

I-5

| Cmpd. No. | R | R$^1$ | R$^9$ |
|---|---|---|---|
| 20 | Cl | Cl | C(=O)OC(CH$_3$)$_3$ |

TABLE 1-continued

Insecticidal 3-(Dihaloalkenyl)phenyl Derivatives where $R^5$ and $R^6$ are chlorine; a is 1; b is 0; E is the bridging group
*—$(CH_2)_i$—$(CH_2)_j$—$(CH_2)_k$—$Q_l$—$(CH_2)_m$—$(CH_2)_n$—$(CH_2)_o$—,
where i, j and k are 1; m, n and o are 0; l is 1; Q is the cyclic moiety

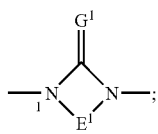

U is X; $R^7$, $R^{10}$ and $R^{11}$ are hydrogen:

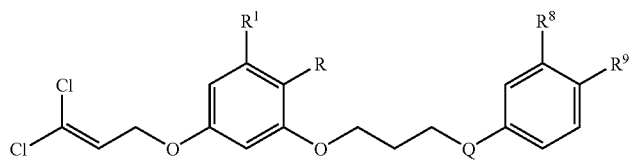

I-6

| Cmpd. No. | R | $R^1$ | Q | $R^8$ | $R^9$ |
|---|---|---|---|---|---|
| 21 | Cl | Cl | ![tetrazolinone] | Cl | H |
| 22 | Cl | Cl | ![triazolinone] | H | $CF_3$ |
| 23 | Cl | Cl | ![triazolinone] | H | $CF_3$ |

TABLE 1-continued

Insecticidal 3-(Dihaloalkenyl)phenyl Derivatives where $R^5$ and $R^6$ are chlorine; a is 0 and b is 0 or 1; E is the bridging group
*—$(CH_2)_i$—$(CH_2)_j$—$(CH_2)_k$—$Q_l$—$(CH_2)_m$—$(CH_2)_n$—$(CH_2)_o$—,
where i, j, k, m, n and o are 0; l is 1; Q is the cyclic moiety

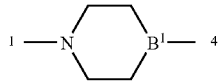

where $B^1$ is —N—; U is T:

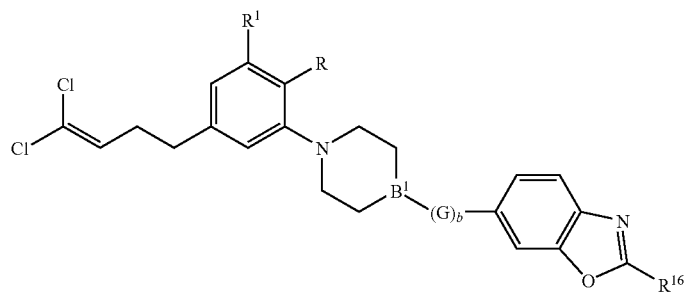

I-7

| Cmpd. No. | R | $R^1$ | $B^1$ | b | G | $R^{16}$ |
|---|---|---|---|---|---|---|
| 24 | Cl | Cl | N | 0 | — | $CF_3$ |
| 25 | Br | Cl | CH | 1 | $CH_2O$ | $CF_3$ |
| 26 | Br | Cl | N | 0 | — | $CF_3$ |
| 27 | Cl | Cl | N | 0 | — | $CH_3$ |
| 28 | Br | Cl | CH | 1 | $CH_2O$ | $CH_3$ |
| 29 | Br | Cl | N | 0 | — | $CH_3$ |
| 30 | Cl | Cl | N | 0 | — | $C(CH_3)_3$ |
| 31 | Br | Cl | CH | 1 | $CH_2O$ | $C(CH_3)_3$ |
| 32 | Br | Cl | N | 0 | — | $C(CH_3)_3$ | where $R^5$ and $R^6$ are chlorine; a and b are each 1; G is —O—; E is the bridging group
*—$(CH_2)_i$—$(CH_2)_j$—$(CH_2)_k$—$Q_l$—$(CH_2)_m$—$(CH_2)_n$—$(CH_2)_o$—,
where i, j, and k are 1; m is 0 or 1; n and o are 0; l is 0; U is T:

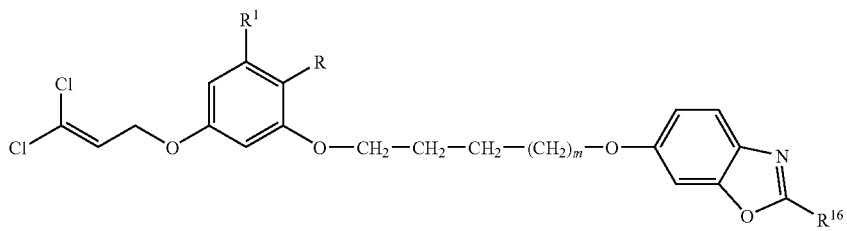

I-8

| Cmpd. No. | R | $R^1$ | m | $R^9$ |
|---|---|---|---|---|
| 33 | Cl | Cl | 0 | $CF_3$ |
| 34 | Cl | Cl | 0 | $CH_3$ |
| 35 | Cl | Cl | 0 | $C(CH_3)_3$ |
| 36 | Cl | Cl | 1 | $CF_3$ |
| 37 | Cl | Cl | 1 | $CH_3$ |
| 38 | Cl | Cl | 1 | $C(CH_3)_3$ |

The following table sets forth physical characterizing data for certain compounds of formula I of the present invention. The test compounds of formula I are identified by numbers that correspond to those in Table 1:

TABLE 2

Insecticidal 3-(Dihaloalkenyl)phenyl Derivatives Characterizing Data

| Cmpd. No. | Empirical Formulae | Physical State (MP ° C.) |
|---|---|---|
| 1 | $C_{22}H_{23}Cl_3O_4$ | Solid |
| 2 | $C_{23}H_{24}Cl_4O_4$ | Liquid |
| 3 | $C_{23}H_{25}Cl_3O_4$ | Solid |
| 4 | $C_{24}H_{26}Cl_4O_4$ | Liquid |
| 5 | $C_{22}H_{22}Cl_4O_4$ | Oil |
| 6 | $C_{19}H_{17}Cl_5O_3$ | Solid |
| 7 | $C_{18}H_{15}Cl_5O_3$ | Oil |
| 8 | $C_{20}H_{19}Cl_5O_3$ | Solid |
| 9 | $C_{21}H_{21}Cl_5O_3$ | Solid |
| 10 | $C_{21}H_{17}Cl_4F_3N_2O_2$ | Liquid |
| 11 | $C_{21}H_{19}Cl_5N_2O_3$ | Liquid |
| 12 | $C_{22}H_{22}Cl_4N_2O_2$ | Liquid |
| 13 | $C_{20}H_{17}Cl_4F_3N_2O$ | 98-101 |
| 14 | $C_{21}H_{20}Cl_4N_2O_2$ | Solid |
| 15 | $C_{21}H_{19}Cl_5N_2O_2$ | Solid |
| 16 | $C_{21}H_{21}Cl_5N_2O_3S$ | Solid |
| 17 | $C_{19}H_{16}Cl_4F_3N_3O$ | 93-96 |
| 18 | $C_{21}H_{19}BrCl_3F_3N_2O_2$ | Oil |
| 19 | $C_{19}H_{16}BrCl_3F_3N_3O$ | Solid |
| 20 | $C_{21}H_{27}Cl_4NO_4$ | Liquid |

Candidate insecticides were evaluated for activity against the tobacco budworm (*Heliothis virescens* [Fabricius]) in a surface-treated diet test.

In this test one mL of molten (65-70° C.) wheat germ-based artificial diet was pipetted into each well of a four by six (24 well) multi-well plate (ID#430345-15__5 mm dia.×17.6 mm deep; Corning Costar Corp., One Alewife Center, Cambridge, Mass. 02140). The diet was allowed to cool to ambient temperature before treatment with candidate insecticide.

For a determination of insecticidal activity, solutions of the candidate insecticides were prepared for testing using a Packard 204DT Multiprobe® Robotic System (Packard Instrument Company, 800 Research Parkway, Meriden, Conn. 06450), in which the robot first diluted a standard 50 millimolar DMSO solution of candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to dry, leaving 0.25 millimoles of candidate insecticide on the surface of the diet, or a concentration of 0.25 millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.25, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed one second instar tobacco budworm larvae, each weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day).

After the five-day exposure period insecticidal activity for each rate of application of candidate insecticide was assessed as percent inhibition of insect weight relative to the weight of insects from untreated controls.

Insecticidal activity data at selected rates of application from this test are provided in Table 3. The test compounds of formula I are identified by numbers that correspond to those in Table 1.

TABLE 3

Insecticidal Activity of Certain 3-(Dihaloalkenyl)phenyl Derivatives When Applied to the Surface of the Diet of Tobacco Budworm (*Heliothis virescens* [Fabricius])

| Cmpd. No. | Percent Growth Inhibition | Cmpd. No. | Percent Growth Inhibition |
|---|---|---|---|
| 1 | 42 | 2 | 100 |
| 3 | 62 | 4 | 100 |
| 5 | 28 | 6 | 55 |
| 7 | 100 | 8 | 8 |
| 9 | 11 | 10 | 48 |
| 11 | 100 | 12 | 61 |
| 13 | 3 | 14 | 99 |
| 15 | 8 | 16 | 81 |
| 17 | 100 | 18 | 17 |
| 19 | 100 | 20 | 98 |

Concentration of the candidate insecticide on the surface of the diet is 0.25 millimolar As set forth in Table 3, compounds tested provided growth inhibition of tobacco budworm. Compounds 2, 4, 7, 11, 17 and 19 provided 100% growth inhibition when compared to the growth of tobacco budworm in untreated controls.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of formula I:

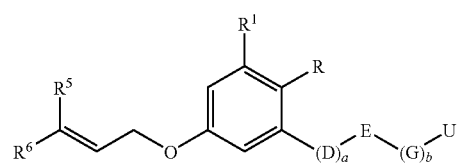

where
R and $R^1$ are independently selected from hydrogen, halogen, alkyl and cyano;
$R^5$ and $R^6$ are independently selected from bromine and chlorine;
a is 0 or 1;
and when a is 1,
D is —O—;
E is a bridging group

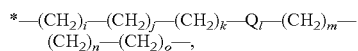

where
the asterisk denotes attachment at D; i, j, k, l, m, n and o are integers independently selected from 0 and 1;
and
when l is 1,
Q is a 5- or 6-membered heterocyclic ring containing from 1 to 4 nitrogen atoms and 0 to 1 oxygen or sulfur atom;
With the proviso that when Q is a cyclic moiety of the structure;

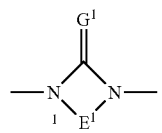

$E^1$ is selected from the group consisting of —$CR^{34}$=$CR^{35}$—, *—$CR^{34}$=N—, *—N=$CR^{34}$—, —N=N—, *—C(=O)$CR^{34}$—, *—$CR^{24}$C(=O)—, —$CR^{34}R^{35}CR^{36}R^{37}$—, *—C(=O)$NR^{34}$—, *—$NR^{34}$C(=O)—, *—S(O)$_s$ $CR^{34}R^{35}$—, *—S(O)$_s NR^{34}$—, *—$OCR^{34}R^{35}$—, *—$CR^{34}R^{35}$—, *—$CR^{34}R^{35}$O— and —C(=O)— where the asterisk denotes attachment to the nitrogen designated as 1 in Q, s is 0, 1 or 2, and $R^{34}$ through $R^{37}$, inclusively, are independently selected from the group consisting of hydrogen, halogen, alkyl, alkoxy, alkoxyalkyl, haloalkyl, alkoxycarbonyl, nitro, cyano, amino, alkylamino and aryl; and
$G^1$ is selected from the group consisting of O, S, N—$J^1$, or C—$J^1$, where $J^1$ is cyano or nitro;
b is an integer selected from 0 or 1;
and, when b is 1,
G is selected from the group consisting of —O—, —$CH_2$O—, —CH=CH—, —S(O)$_h$—, —S(O)$_h$ $CH_2$—, —S(O)$_h C_2 H_4$—, —HC=N—, —C(=O)—, —OC(=O)—, —C(=O)O—, —C(=O)$C_2 H_4$—, —C(=O)$OCH_2$—, —C(=O)$CH_2$—, —C(=O)NH—, —$NR^{14}$—, —N(oxide)$R^{14}$— and —$NR^{14}$C(=O)— where h is 0, 1 or 2 and $R^{14}$ is selected from the group consisting of hydrogen, alkyl, alkoxyalkyl, arylalkyl, alkenylalkyl, haloalkenylalkyl, dialkylphosphonate, alkylcarbonyl, haloalkylcarbonyl, alkoxyalkylcarbonyl, arylcarbonyl and alkylsulfonyl;
U is selected from the group consisting of:

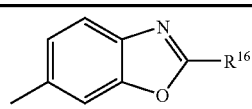
T,

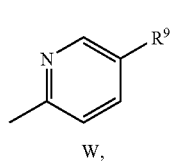
W,

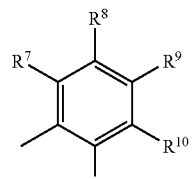
X,

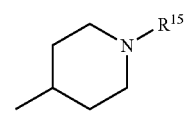
Y and

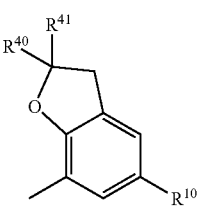
Z;

where;
$R^7$, $R^8$, $R^{10}$ and $R^{11}$ are independently selected from the group consisting of hydrogen and halogen;
$R^9$ selected from the group consisting of hydrogen, halogen and haloalkyl;
$R^{15}$ is alkoxycarbonyl;
$R^{16}$ is selected from the group consisting of alkyl and haloalkyl;
$R^{40}$ and $R^{41}$ are each, independently, alkyl;
provided that when (a) R, $R^1$, $R^5$ and $R^6$ are chlorine; (b) a, i, j, k, n, and o are 0; (c) $B^1$ is —CH—; (d) m is 1 and (e) U is group X where $R^7$ through $R^{11}$ are hydrogen, then b is 1;
and
agriculturally acceptable salts thereof.

2. A compound of claim 1 where
Q is a cyclic moiety of the structure;

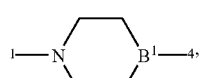

where,
1- and 4- denote points of attachment to the —$(CH_2)_k$— and to the —$(CH_2)_m$— sides of bridging group L; $B^1$ is —N— or —CH—;

or
Q is a cyclic moiety of the structure;

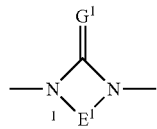

where
E$^1$ is selected from the group consisting of —CR$^{34}$=CR$^{35}$—, *—CR$^{34}$=N—, *—N=CR$^{34}$—, —N=N—, *—C(=O)CR$^{34}$—, *—CR$^{24}$C(=O)—, —CR$^{34}$R$^{35}$CR$^{36}$R$^{37}$—, *—C(=O)NR$^{34}$—, *—NR$^{34}$C(=O)—, *—S(O)$_s$CR$^{34}$R$^{35}$—, *—S(O)$_s$NR$^{34}$—, *—OCR$^{34}$R$^{35}$—, *—CR$^{34}$R$^{35}$O— and —C(=O)— where the asterisk denotes attachment to the nitrogen designated as 1 in Q, s is 0, 1 or 2, and R$^{34}$ through R$^{37}$, inclusively, are independently selected from the group consisting of hydrogen, halogen, alkyl, alkoxy, alkoxyalkyl, haloalkyl, alkoxycarbonyl, nitro, cyano, amino, alkylamino and aryl; and
G$^1$ is selected from the group consisting of O, S, N—J$^1$, or C—J$^1$, where J$^1$ is cyano or nitro.

3. A compound of claim 1 where when l is 1;
Q is a cyclic moiety of the structure

where,
1- and 4- denote points of attachment to the —(CH$_2$)$_k$— and to the —(CH$_2$)$_m$— sides of bridging group E; B$^1$ is —N— or —CH—;
or
Q is a cyclic moiety of the structure;

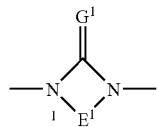

where
E$^1$ is selected from the group consisting of *—CR$^{34}$=N—, *—N=CR$^{34}$—, and —N=N— where the asterisk denotes attachment to the nitrogen designated as 1 in Q, and R$^{34}$ is selected from the group consisting of hydrogen, halogen, alkyl, alkoxy, alkoxyalkyl, haloalkyl, alkoxycarbonyl, nitro, cyano, amino, alkylamino and aryl;
b is an integer selected from 0 or 1;
and, when b is 1,
G is selected from —O—, —CH$_2$O—, —S(O)$_2$C$_2$H$_4$—, —C(=O)—, —C(=O)OCH$_2$—, —(C=O)CH$_2$— and —C(=O)C$_2$H$_4$—.

4. A compound of claim 3 where
R and R$^1$ are each, independently, halogen;
a, b, i, j, k, m, n and o are each 0;
l is 1; Q is a cyclic moiety of the structure

where B$^1$ is N;
and
U is W and R$^9$ is halogen.

5. A compound of claim 3 where
R and R$^1$ are each, independently, halogen;
a, i, j, k m, n and o are each 0;
l is 1; Q is a cyclic moiety of the structure

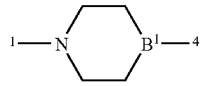

where B is N;
b is 1; G is selected from the group consisting of —C(=O)OCH$_2$—, —C(=O)—, —C(=O)CH$_2$—, —C(=O)C$_2$H$_4$— and —SO$_2$C$_2$H$_4$—;
U is X; and R$^8$, R$^{10}$ and R$^{11}$ are hydrogen.

6. A compound of claim 3 where
R and R$^1$ are independently hydrogen or halogen;
a and b are each 1 and G is —O—;
l and o are each 0; i, j, k are each 1; m and n are independently selected from 0 and 1;
and
U is Z.

7. A compound of claim 3 where
R and R$^1$ are each, independently, halogen;
a and b are each 1 and G is —O—;
l is 0; i, j and k are each 1; m, n and o are independently selected from 0 and 1;
and
U is X; R$^7$, R$^8$, R$^{10}$ and R$^{11}$ are hydrogen and R$^9$ is halogen.

8. A compound of claim 3 where
R and R$^1$ are each, independently, halogen;
a, i, j, k m, n and o are each 0;
l is 1; Q is a cyclic moiety of the structure

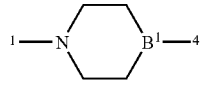

where B$^1$ is —CH—;
b is 1 and G is —CH$_2$O—;
U is W and R$^9$ is haloalkyl.

9. A compound of claim 3 where
R and R$^1$ are each, independently, halogen;
a is 1;
i and j are each 1 and k, l, m, n and o are 0;
b is 0;
and
U is Y.

10. A compound of claim 3 where
R and R$^1$ are each, independently, halogen;
a, b, i, j, k, m, n and o are each 0;
l is 1; Q is a cyclic moiety of the structure

where $B^1$ is —N—;
and
U is X; $R^7$, $R^8$, $R^{10}$ and $R^{11}$ are hydrogen and $R^9$ is haloalkyl.

11. A composition comprising an insecticidally effective amount of a compound of claim 1 in admixture with at least one agriculturally acceptable extender or adjuvant.

12. The insecticidal composition of claim 11, further comprising one or more additional compounds selected from the group consisting of pesticides, plant growth regulators, fertilizers and soil conditioners.

13. A method of controlling insects, comprising applying an insecticidally effective amount of a composition of claim 11 to a locus where insects are present or are expected to be present.

14. A method of controlling insects, comprising applying an insecticidally effective amount of a composition of claim 12 to a locus where insects are present or are expected to be present.

* * * * *

UNITED STATES PATENT AND TRADEMARK OFFICE
CERTIFICATE OF CORRECTION

PATENT NO. : 7,671,055 B2  Page 1 of 1
APPLICATION NO. : 11/577667
DATED : March 2, 2010
INVENTOR(S) : Edward J. Barron et al.

It is certified that error appears in the above-identified patent and that said Letters Patent is hereby corrected as shown below:

Column 33, line 27, delete "*-CR34R35-"

Column 34, line 66, change "group L;" to --group E;--

Column 36, line 21, change "where B" to --where B1--

Signed and Sealed this

Twenty-fifth Day of May, 2010

David J. Kappos
*Director of the United States Patent and Trademark Office*